US006235001B1

(12) United States Patent
O'Holloran et al.

(10) Patent No.: US 6,235,001 B1
(45) Date of Patent: May 22, 2001

(54) SURGICAL NEEDLE WITH HAND-ACTUABLE LOCK MECHANISM

(76) Inventors: Brian O'Holloran, 2275 NE. Doctor's Dr., Bend, OR (US) 97701; Patrick J. Ferguson, P.O. Box 6724, Portland, OR (US) 97208

( * ) Notice: Subject to any disclaimer, the term of this patent is extended or adjusted under 35 U.S.C. 154(b) by 0 days.

(21) Appl. No.: 09/313,881

(22) Filed: May 18, 1999

(51) Int. Cl.[7] ................................................. A61M 5/178
(52) U.S. Cl. ................... 604/165.02; 604/164.07
(58) Field of Search .................... 604/164, 165, 604/528, 117, 187, 192, 198, 263, 159, 164.04, 164.07, 164.13, 165.01, 165.02; 606/172

(56) References Cited

U.S. PATENT DOCUMENTS

| 4,013,080 | * | 3/1977 | Froning ........................ 604/165.01 |
| 4,461,280 | | 7/1984 | Baumgartner . |
| 4,700,692 | | 10/1987 | Baumgartner . |
| 4,815,449 | | 3/1989 | Horowitz . |
| 4,969,879 | * | 11/1990 | Lichte ................................. 604/533 |
| 5,041,085 | | 8/1991 | Osborne et al. . |
| 5,207,647 | | 5/1993 | Phelps . |
| 5,242,427 | | 9/1993 | Bilweis . |
| 5,290,304 | | 3/1994 | Storace . |
| 5,368,046 | | 11/1994 | Scarfone et al. . |
| 5,399,165 | | 3/1995 | Paul . |
| 5,556,411 | | 9/1996 | Taoda et al. . |
| 5,836,914 | * | 11/1998 | Houghton ........................... 604/117 |

OTHER PUBLICATIONS

Advertisement for "Performance Plus Needle Sentry," by Standard Imaging of Middleton, Wisconsin, Oct. 15, 1998.

* cited by examiner

Primary Examiner—Anhtuan T. Nguyen
(74) Attorney, Agent, or Firm—Kolisch Hartwell Dickinson McCormack & Heuser

(57) ABSTRACT

A surgical needle assembly including a hollow needle body, a push rod slidingly fit within the hollow needle body, and a hand-actuable lock mounted on the needle body. The lock selectively limits movement of the push rod relative to the needle body in response to a squeezing or releasing of the lock.

26 Claims, 4 Drawing Sheets

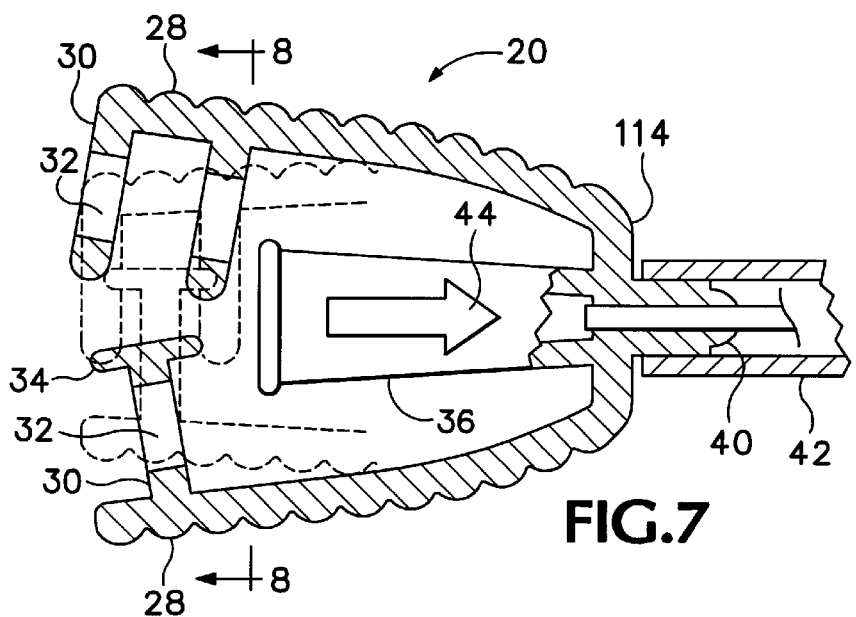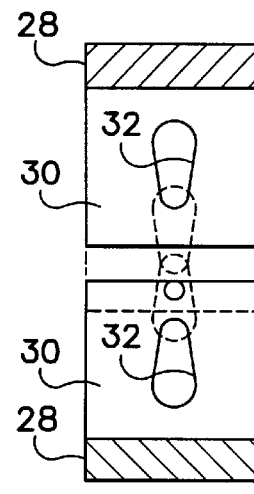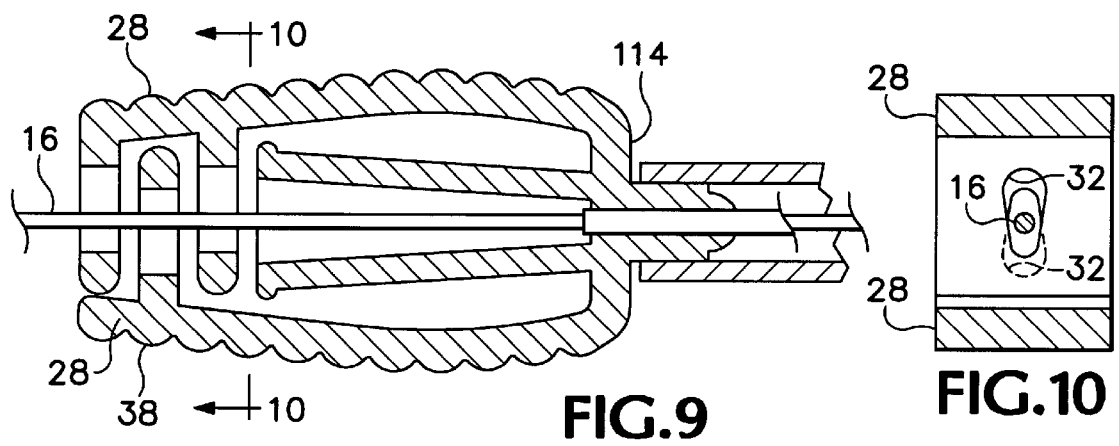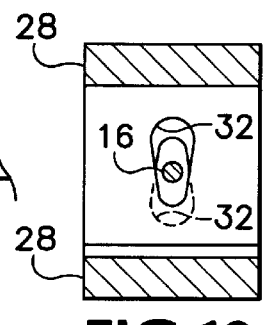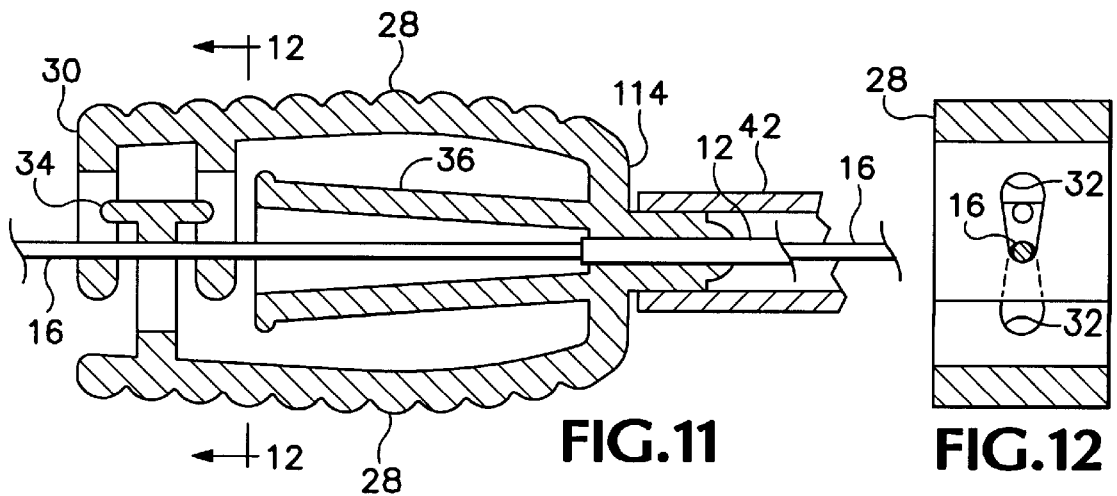

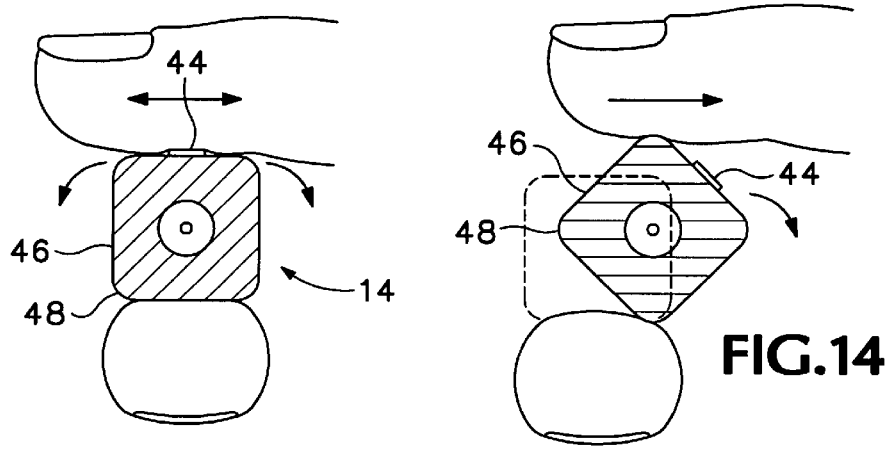
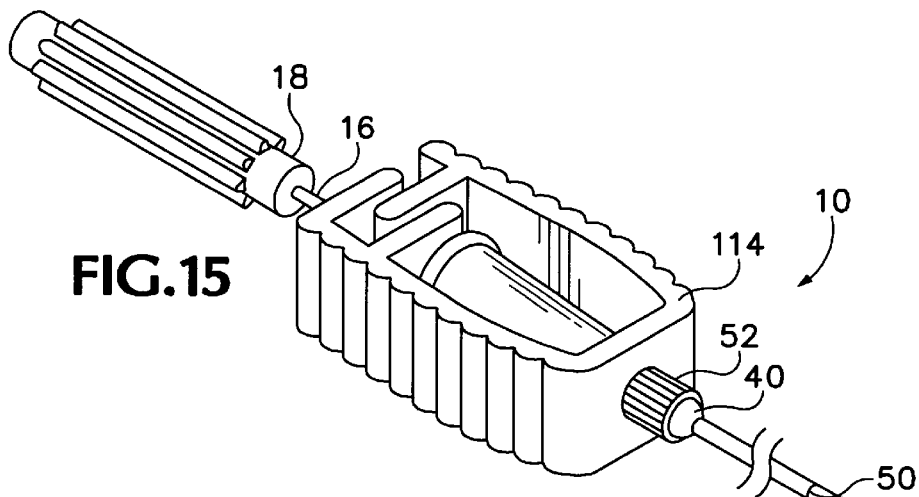
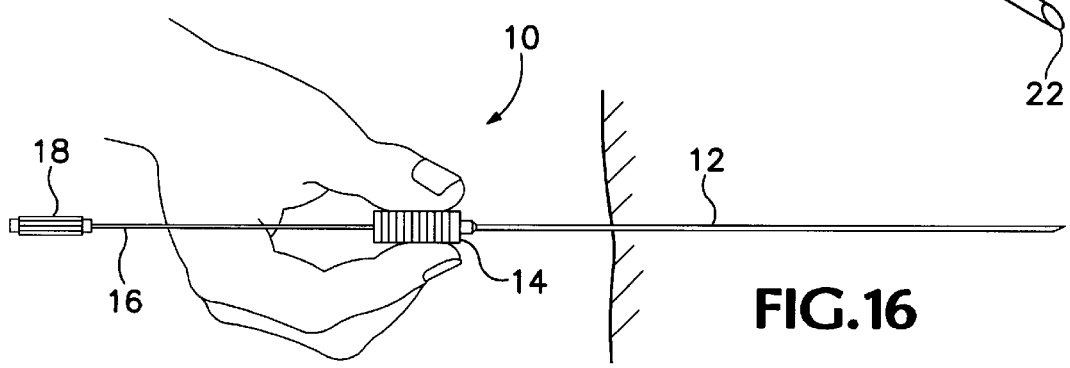

SURGICAL NEEDLE WITH HAND-ACTUABLE LOCK MECHANISM

BACKGROUND OF THE INVENTION

This invention relates generally to surgical tools and, more specifically, to a surgical needle with a hand-actuable lock mechanism for holding one part of the needle approximately fixed relative to another part. One embodiment of the needle includes a hollow needle through which a push rod slides, and the lock is used to hold the push rod fixed relative to the hollow needle. Such hollow needle/push rod assemblies often are used when depositing, sampling or removing material within living tissue.

The lock mechanism of the present invention may be mounted on various types of needles, push rods, catheters, stents, trocars, cannulas, wires and stylets. The detailed description of the invention, below, is based on an embodiment that may be used in prostate brachytherapy, in which radioactive seeds are implanted in a human prostate while the needle and seeds are monitored by ultrasound sensors and imaging devices. U.S. Pat. Nos. 4,461,280, 4,700,692 and 4,815,449, the disclosures of which are incorporated herein by reference, disclose background information about the deposition of radioactive seeds within human tissue.

The lock mechanism may be used with other known surgical tools, such as trocar and cannula assemblies, in which an inner member such as a rod or inner hollow needle slidingly fits within and extends through an outer hollow needle to block or interact with an open end of the outer needle. For example, fluid and tissue samples may be taken from a specific part of the body by penetrating the desired part of the body with the end of a needle, and then removing a rod from within the needle to open a hollow cavity in the needle and admit fluid or tissue. A syringe or other injection device may also or alternatively be attached to the needle if fluids or solids are to be injected. Examples of such tools are found in U.S. Pat. Nos. 5,207,647, 5,242,427, 5,290,304, 5,368,046, and 5,556,411, the disclosures of which are incorporated herein by reference.

SUMMARY OF THE INVENTION

The lock of the present invention will be described with reference to a surgical needle that includes a hollow, sharp, pointed needle that extends from a grip, mounted on the needle. A push rod extends through the hollow needle to push material through the needle, and the lock is operatively connected to both the needle and rod to lock the rod relative to the needle. The lock is formed as part of the grip, and is shaped so that a surgeon may hold and direct the point of the needle, and lock and unlock the lock to selectively limit movement of the push rod relative to the needle.

This embodiment of the needle may be loaded with material such as radioactive seeds to be deposited within living tissue. When so loaded, the needle assembly is in a loaded position. The material contained within the needle assembly may be extruded by moving either the push rod or the hollow needle relative to the other. When the push rod is inserted fully into the hollow needle, the needle assembly is in an empty position.

The needle and push rod may be used collectively to deposit material in living tissue, preferably by inserting the needle loaded with material into the tissue. The push rod then is held in a fixed position relative to the tissue and the needle is slid back over the push rod, forcing material out of the needle as the needle is withdrawn from the tissue. By carefully controlling the relative motion of the push rod to the needle, material may be distributed through the tissue as desired, typically along a line traced by the point of the needle as it is withdrawn from the tissue.

The lock mechanism preferably may be controlled by squeezing and releasing the grip. For example, the lock mechanism may be unlocked when the grip is squeezed, and locked when the grip is not squeezed. This has been found to be particularly useful for surgical procedures, because the surgeon will need to have a hand on the device to control its relative motion anyway, and the squeezing of the lock does not limit the surgeon's ability to maneuver the needle.

When the lock of the assembly is unlocked, the needle preferably slides freely relative to the push rod. In one embodiment of the invention, the lock mechanism is formed by fingers that extend toward the push rod from outwardly biased arms of the grip. Holes are formed within the fingers, oversized relative to the push rod so that it may slide freely through the holes when the arms are squeezed.

The advantages of the present invention and its various embodiments will be understood more readily after a consideration of the drawings and the Detailed Description of the Preferred Embodiment.

BRIEF DESCRIPTION OF THE DRAWINGS

FIG. 7 is a greatly enlarged plan view of the grip portion of the assembly shown in FIGS. 4–6, without a push rod inserted into the grip and needle portions, and with a locked position of the arms of the grip shown in dashed lines and a protective sheath shown in cross section.

FIG. 8 is a cross-sectional view of the grip shown in FIG. 8, taken along line 8—8 in FIG. 7, shown on approximately the same scale as in FIG. 7.

FIG. 9 is a cross-sectional view of the grip portion of the assembly shown in FIGS. 4–6, taken from a point of view similar to that in FIG. 7, with a push rod inserted into the grip and needle portions, and with the lock of the assembly squeezed so that the push rod slides freely relative to the needle, shown on approximately the same scale as in FIG. 7.

FIG. 10 is a cross-sectional view of the grip shown in FIG. 9, taken along line 10—10 in FIG. 9, shown on approximately the same scale as in FIG. 7.

FIG. 11 is a cross-sectional view of the grip portion of the assembly shown in FIGS. 4–6, taken from a point of view similar to that in FIG. 7, with a push rod inserted into the grip and needle portions, and with the needle locked relative to the push rod so that the needle does not slide freely relative to the push rod, shown on approximately the same scale as in FIG. 7.

FIG. 12 is a cross-sectional view of the grip shown in FIG. 11, taken along line 12—12 in FIG. 11, shown on approximately the same scale as in FIG. 7.

FIG. 13 is a cross-sectional view of the grip shown in FIG. 1, taken along line 13—13 in FIG. 1, shown on approximately the same scale as in FIG. 7.

FIG. 14 is a cross-sectional view of the grip shown in FIG. 13, rotated about the long axis of the needle.

FIG. 15 is an isometric view of the alternative embodiment of the needle assembly of FIGS. 4–12.

FIG. 16 is a view of the needle assembly embodiment of FIG. 16, viewed similarly to FIG. 1, with the needle in its loaded position, inserted into living tissue.

DETAILED DESCRIPTION OF THE PREFERRED EMBODIMENT

Figure 1:
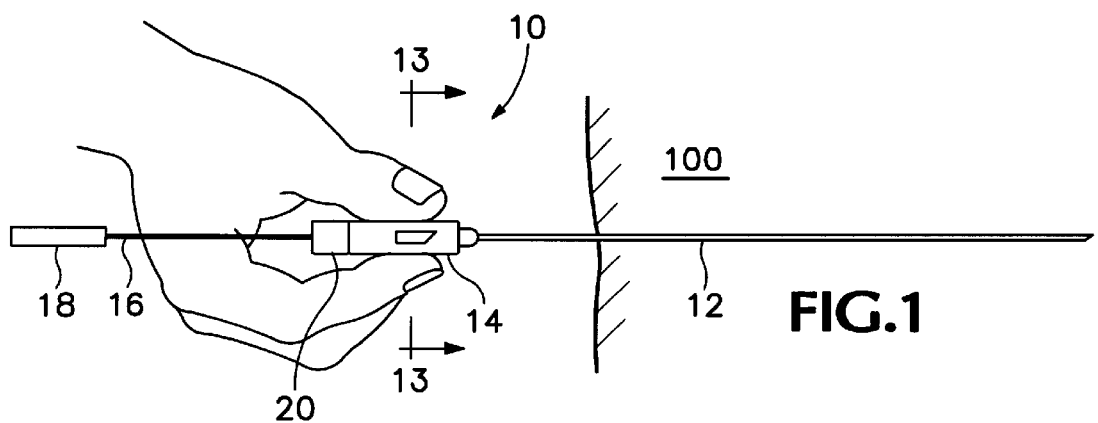
FIG. 1 is a view showing a needle assembly according to the present invention being inserted into living tissue, with the needle assembly in its loaded position.

Referring to FIG. 1, a surgical needle assembly 10 according to the present invention is shown inserted into a portion of a human body 100. Assembly 10 includes an open-ended, hollow needle 12, also referred to as a slender outer tube or delivery tube. A grip 14 is mounted on or attached to one end of needle 12 so that needle 12 may be manipulated easily by a human hand. A push rod 16 extends through needle 12 to form a type of plunger or piston, as described in more detail below. A handle 18 is formed on the end of rod 16, so that rod 16 may be manipulated by a human hand, separately or in conjunction with the manipulation of needle 12. Preferably, needle 12 and push rod 16 are made of surgical grade stainless steel, and grip 14 and handle 18 are made of medical grade polycarbonate, but other metals, plastics and composites may be used.

Figure 2:
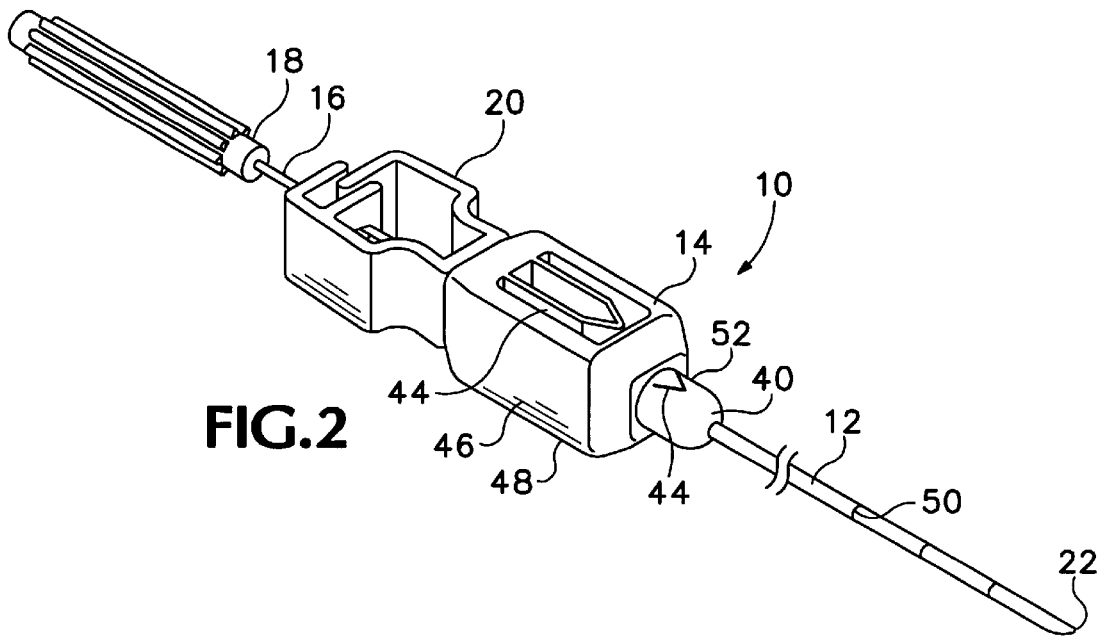
FIG. 2 is an enlarged isometric view of the needle assembly of FIG. 1, shown in its empty position.

Referring to FIG. 2, assembly 10 is shown in isometric view, with portions of needle 12 and rod 16 removed to fit the image of the assembly within the drawing page. Grip 14 includes a lock 20 to hold rod 16 relative to needle 12 by frictional forces between lock 20 and rod 16, when the moving elements of lock 20 are allowed to move outwardly to an unsqueezed position. Rod 16 is therefore locked so that it does not slip into or out of needle 12. When lock 20 is squeezed, as shown in dashed lines in FIG. 2, the frictional forces are removed, so that rod 16 slips freely relative to needle 12. This allows rod 16 to be used as a push rod to push out any material stored in hollow needle 12.

Figure 3:
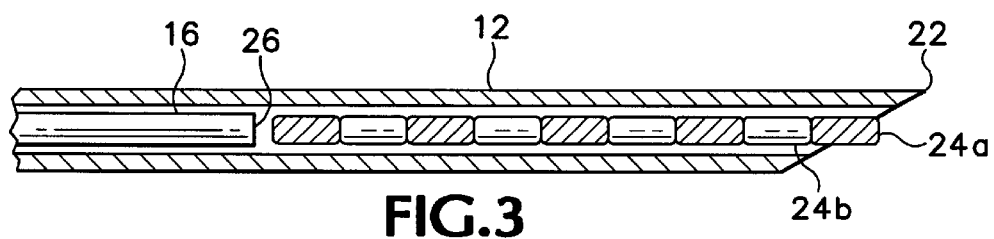
FIG. 3 is a greatly enlarged cross-sectional view of the end portion of the assembly shown in FIGS. 1 and 2, shown in a loaded position, with the push rod and radioactive seeds contained within the needle not cross-sectioned.

Still referring to FIG. 2, a sharp point 22 is formed at the end of needle 12 to pierce and penetrate the flesh and tissue of a human body, so that needle 12 may be used as a delivery tube to deliver material to within the flesh or tissue of a human body. For example, in FIG. 3 details of such material loaded in needle 12 are shown in a greatly enlarged cross-sectional view. Radioactive seeds 24a and spacers 24b, referred to collectively as seeds 24, are held within hollow needle 12, ready for delivery to a diseased prostrate. Rod 16 includes a blunt end 26 that may be used to push seeds 24 relative to needle 12, and thereby force seeds 24 out of needle 12 as desired.

An alternative embodiment of the surgical needle assembly of the present invention is shown in FIGS. 4 through 12, 15 and 16. Assembly 10 includes a needle 12 and push rod 16 as in the embodiment of FIGS. 1 through 3, 13 and 14, but is formed with a grip 114 that is shorter than grip 14 of FIGS. 1–3. However, care must be exercised when using the embodiment of FIGS. 4 through 12 not to inadvertently squeeze lock 20, thereby unlocking rod 16 relative to needle 12. For example, it has been found best to hold assembly 10 as shown in FIG. 16 to avoid unlocking rod 16.

In FIGS. 1, 4, 5, and 6, assembly 10 is shown in use to deliver seeds 24, just discussed. Beginning with FIG. 1, needle 12 is inserted into the flesh and tissue of a human body 100 to a desired point, while lock 20 is in its biased, locked position to hold rod 16. This prevents undesired movement of rod 16 relative to needle 12.

Figure 4:
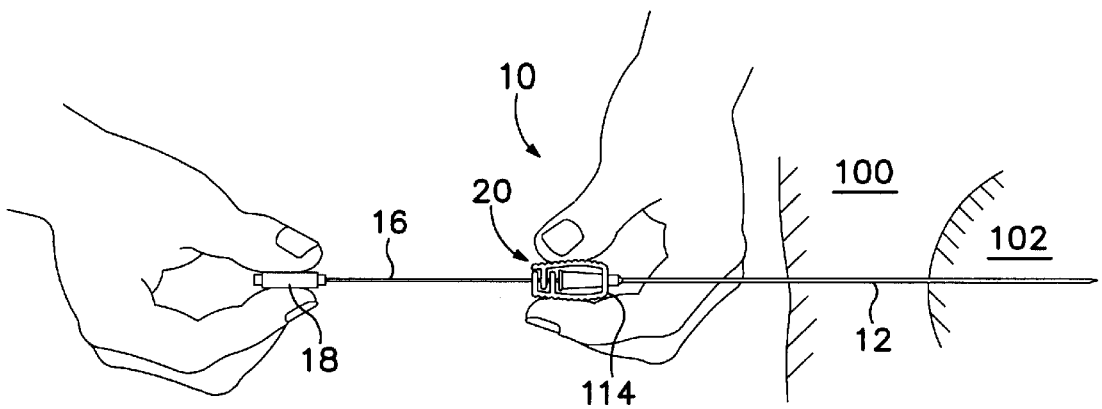
FIG. 4 is a view showing an alternative embodiment of the needle assembly of FIG. 1 after it has been inserted into living tissue as far as desired, with the lock of the assembly squeezed so that the needle slides freely relative to the push rod.
Figure 5:
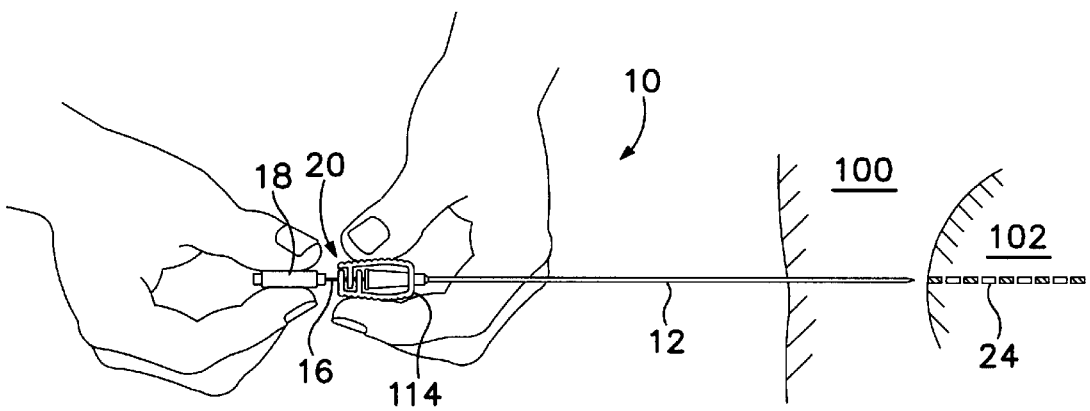
FIG. 5 is a view showing the needle assembly of FIG. 4 after the needle has been withdrawn from the living tissue as far as desired while holding the push rod stationary relative to the living tissue, leaving a trail of seeds within the tissue, with the lock of the assembly squeezed so that the needle slides freely relative to the push rod.

After insertion to the desired point, for example within a prostate 102, as shown in FIG. 4, the operator's hands may be readjusted to a position suitable for depositing seeds 24 within prostate 102. Lock 20 may be held in an unlocked position by one hand (left hand shown), while handle 18 of rod 16 is held by the other hand (right hand shown). While squeezing lock 20 to unlock the locking mechanism, as shown in FIG. 5, and while holding handle 18 of rod 16 steady relative to tissues 100, needle 12 is withdrawn from tissues 100. Alternatively, two surgeons may perform the procedure as a team, with one surgeon holding handle 18, while the other surgeon withdraws needle 12.

As needle 12 is withdrawn, radioactive seeds 24 are forced out of needle 12 by blunt end 26 of rod 16. Because needle 12 moves and rod 16 and seeds 24 remain essentially stationary relative to body 100 during this step of the procedure, seeds 24 are deposited in a line corresponding to the prior location of needle 12. As used herein, "line" may be more or less precise, depending on the type of material deposited in body 100, the properties of the tissue in which the line is deposited, the skill of the surgeon operating assembly 10, and other factors. A deposited line may also be straight or curved, regular or irregular, based on similar factors and based on the flexibility of needle 12 and rod 16.

Figure 6:
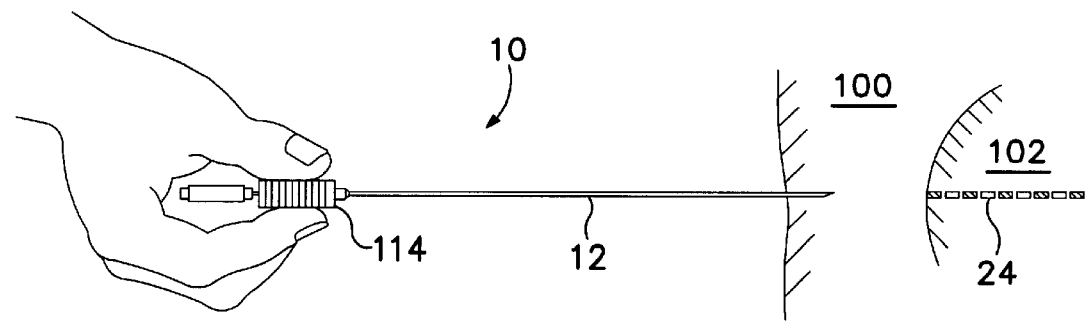
FIG. 6 is a view showing the needle assembly of FIG. 5 being removed from the living tissue, with the needle locked relative to the push rod so that no additional seeds are deposited into the tissue as the assembly is removed.

Once a desired amount of seeds 24 have been deposited in body 100, or once needle 12 has been withdrawn a desired amount from body 100, the squeezing pressure on lock 20 is removed. This locks rod 16 relative to needle 12, so that needle 12 and rod 16 may be removed without pushing additional radioactive seeds 24 out of needle 12, as shown in FIG. 6. If desired, the hand position on assembly 10 may be changed for this final removal step, as shown in FIG. 6.

Referring now to FIGS. 7 through 12, lock 20 and other features of device 10 will be described in detail. In FIG. 7, lock 20 is shown prior to the insertion of rod 16 into needle 12. Lock 20 includes a spring in the form of a pair of outwardly extending, resiliently biased arms 28, molded from a resilient material such as the polycarbonate preferred for grips 14 or 114, so that the natural, unsprung position of the arms is splayed outwardly, as shown in FIG. 7. When arms 28 are squeezed together to allow rod 16 to be inserted, arms 28 are springs that press outwardly relative to rod 16, toward the arms' natural unsprung position.

Polycarbonate is preferred because it tends to retain its shape memory over time, even if arms 28 are left in an inward position such as that shown in FIG. 9. Other materials, such as nylon or polypropylene, tend to assume the inward position, so that the effectiveness of lock 20 is lost over time. Regardless of the material used, it is best to leave arms 28 in an extended, outward position as shown in FIG. 7, until the time of use of assembly 10.

Each arm 28 includes at least one inwardly extending finger 30, and each finger 30 includes a hole or passageway 32, preferably a tapered hole that is teardrop-shaped as shown in FIG. 8. Preferably, one arm 28 includes a pair of fingers 30, and the other arm 28 includes a single finger 30 having tabs 34 extending outwardly near the tapered end of hole 32. Tabs 34 fit within and interlock with holes 32 of the pair of fingers 30, to hold arms 28 in a partially closed, compressed position, as shown in dashed lines in FIG. 7. This has been found to help in inserting rod 16 through holes 32 when assembling assembly 10, particularly if this must be done after needle 12 has been inserted into tissue 100.

In FIGS. 9 and 10, arms 28 are shown squeezed together toward rod 16, so that the enlarged portions of holes 32 overlap and limited or no contact occurs between rod 16 and holes 32. Thus the locking mechanism is unlocked, allowing free passage of rod 16 through holes 32. The inward movement of arms 28 is limited by the length of fingers 30, which are stopped by an opposing arm 28 when arms 28 are squeezed toward one another to a fully squeezed position. When arms 28 are not squeezed, rod 16 is locked by the tapered portions of holes 32, as shown in FIGS. 11 and 12. This releasable locking mechanism provides sufficient holding force for the operation described above with respect to FIGS. 1, 4, 5, and 6. It is selectively actuable by the surgeon using very simple hand movements, and does not interfere with the surgeon's control of the placement of needle 12 within body 100.

Holes 32 include V-shaped locking surfaces formed as part of the teardrop-shape of holes 32, shown best in FIG. 8. These V-shaped locking surfaces are believed to provide reliable locking and unlocking performance of lock 20, particularly in those embodiments in which oppositely biased arms 28 each include V-shaped locking surfaces, so that the opposing locking surfaces are forced in opposite directions by the spring of arms 28, each toward rod 16 held within needle 12. However, other shapes may be used with satisfactory results, and perhaps even with superior results. For example, holes 32 may be round, oval, square or triangular, with or without a V-shaped or other taper in the locking surfaces relative to the movement of hole 32 with respect to rod 16. Furthermore, the size of hole 32 relative to finger 30 may be such that substantial locking, frictional contact is made with rod 16 at both an unsqueezed and a fully squeezed position of arm 28, so that rod 16 may be locked in both the unsqueezed and squeezed positions of arm 28. Limited or no contact is made between rod 16 and hole 32 in an intermediate, unlocked position of arm 28.

Other aspects of grip 114 are identified in FIG. 7, including a funnel 36 that acts as a guide for feeding seeds 24 into needle 12. The interconnection between funnel 36 and needle 12 is seen best in FIG. 11. Funnel 36 also guides blunt end 26 of rod 16 when inserting rod 16 into needle 12.

Also shown in FIG. 7 is a gripping texture 38 formed on arms 28, preferably corrugated. Finally, a bushing 40 provides a reinforcement for joining grip 114 to needle 12, and doubles as a plug for receiving a protective sheath 42, used when storing and handling assembly 10. Sheath 42 preferably is at least as long, if not longer, than needle 12, protecting against inadvertent punctures and injuries by needle 12.

Referring again to FIG. 2, indicia 44 formed on grip 14 provide a visual indication of the orientation of point 22 of needle 12 relative to grip 14. This is important because the unidirectionally taper formed by the sloped cut of the point tends to drive the point in a particular direction within a body 100, relative to the long axis of needle 12. A surgeon may use this tendency to position needle 12 accurately within a body 100. Indicia 44 may simply be printed on grip 14, or, as shown in FIG. 2, may be formed with sufficient structural relief that indicia 44 provides a tactile as well as a visual indication of orientation.

The shape of grip 14 shown in FIGS. 2, 13 and 14 also helps a user of assembly 10 position needle within a body 100. Relatively flat surfaces 46 provide a tactile indicator of the location of the point of needle 12, or at least that the point is at 0-, 90-, 180-, or 270-degrees relative to a particular surface 46. The exact orientation is confirmed by feeling or looking at indicia 44. Grip 14 is formed with slightly rounded corners 48 that roll easily when gripped, allowing a surgeon to rotate needle 12 about its long axis, as shown in FIG. 14.

Referring once again to FIG. 2, markings 50 may be provided on needle 12, preferably in one-centimeter increments, with every five-centimeters marked or accented, as shown. Similar markings may be applied to rod 16. Bushing 40 is shown to include ribs 52 that help retain protective sheath 42, discussed above, and to include indicia 44.

The foregoing description of the preferred embodiment of the invention has been presented for purposes of illustration and description. It is not intended to be exhaustive or to limit the invention to the precise form disclosed, and many modifications and variations are possible in light of the above teaching. The embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined only by the scope of the issued claims.

What is claimed is:

1. A surgical needle comprising:

an outer tube;

an inner member slidingly fit within the outer tube; and a lock mounted on the outer tube, including a pair of arms biased outwardly relative to the inner member that each extend from the outer tube and are positioned generally on opposite sides of the inner member, at least one of the arms including a finger extending inwardly toward the inner member, the finger having a hole oversized relative to the inner member and through which the inner member extends, so that frictional forces may be exerted between the inner member and the finger when the arms are allowed to move outwardly to an unsqueezed position, and so that the frictional forces may be released by squeezing the arms toward the inner member, wherein the lock selectively limits movement of the inner member relative to the outer tube in response to a squeezing or releasing of the arms.

2. The needle of claim 1, wherein the hole and finger are sized such that limited or no contact occurs between the finger and the inner member when the arms are squeezed toward the inner member.

3. The needle of claim 1, wherein the hole and finger are sized such that frictional contact with the inner member occurs when the arms are squeezed toward one another to a fully squeezed position, so that the inner member may be locked in both the unsqueezed position and the fully squeezed position of the arms.

4. The needle of claim 1, wherein the hole includes a surface that is approximately V-shaped.

5. A surgical tool for depositing material within living tissue, comprising:

a delivery tube for penetrating living tissue and delivering material to within living tissue;

an inner member held within the delivery tube to push material through the tube; and a releasable lock operatively connected to the tube, the lock including a pair of resilient arms biased outwardly relative to the inner member that are squeezed toward each other and released to selectively engage the inner member and selectively limit movement of the inner member relative to the tube, at least one of the arms including a finger extending inwardly toward the inner member, the finger having a hole oversized relative to the inner member and through which the inner member extends, so that frictional forces may be exerted between the inner member and the finger when the arms are allowed to move outwardly to an unsgueezed position, and so that the frictional forces may be released by squeezing the arms toward the inner member.

6. The surgical tool of claim 5, wherein a locking surface is formed on a portition of the finger that defines the hole.

7. The surgical tool of claim 6, wherein the hole is sized such that limited or no contact occurs between the locking surface and the inner member when the arms are squeezed toward one another to a filly squeezed position.

8. The surgical tool of claim 6, wherein the hole is sized such that frictional contact with the inner member occurs when the arms are squeezed toward one another to a fully squeezed position, so that the inner member may be locked in both the unsqueezed position and the fully squeezed position of the arms.

9. The surgical tool of claim 6, wherein the locking surface is approximately V-shaped.

10. The surgical tool of claim 6, further comprising a tab formed on the finger, and wherein the tab interlocks the arms to hold the arms in a partially closed position.

11. The surgical tool of claim 5, wherein the lock includes a spring for holding the lock in a biased, locking position.

12. A surgical tool for depositing material within living tissue, comprising:

a delivery tube for penetrating living tissue and delivering material to within living tissue;

an inner member held within the delivery tube to push material through the tube;

a releasable lock operatively connected to the tube to selectively limit movemnent of the inner member relative to the tube, wherein the lock includes outwardly biased arms and locking surfaces formed on fingers extending inwardly from the arms; and a tab formed on at least one of the fingers, and wherein the tab interlocks with a hole on an opposing finger to hold the arms in a partially closed position.

13. A surgical needle comprising:

an outer tube;

an inner member slidingly fit within the outer tube; and a lock mounted on the outer tube, including a pair of arms, at least one of the arms including a finger that extends inwardly toward the inner member and has a hole oversized relative to the inner member through which the inner member extends, where frictional forces are selectively exerted between the inner member and the finger in response to a squeezing and releasing of the arms.

14. The needle of claim 13, wherein the arms are biased outwardly relative to the inner member.

15. The needle of claim 14, wherein the frictional forces are exerted when the arms are allowed to move outwardly to an unsqueezed position, and are released by squeezing the arms toward the inner member.

16. The needle of claim 13, wherein the hole and finger are sized such that limited or no contact occurs between the finger and the inner member when the arms are squeezed toward the inner member.

17. The needle of claim 13, wherein the hole and finger are sized such that frictional contact with the inner member occurs when the arms are squeezed toward one another to a fully squeezed position, so that the inner member may be locked in both an unsqueezed position and the fully squeezed position of the arms.

18. The needle of claim 13, wherein the hole includes a surface that is approximately V-shaped.

19. A surgical tool for depositing material within living tissue, comprising:

a delivery tube for penetrating living tissue and delivering material to within living tissue;

an inner member held within the delivery tube to push material through the tube; and a releasable lock operatively connected to the tube, the lock including a pair of resilient arms, at least one of the arms including a finger that extends inwardly toward the inner member and has a hole oversized relative to the inner member through which the inner member extends, where the arms are squeezed toward each other and released to selectively engage the inner member and selectively limit movement of the inner member relative to the tube.

20. The surgical tool of claim 19, wherein the arms are outwardly biased.

21. The surgical tool of claim 19, wherein a locking surface is formed on a portion of the finger that defines the hole.

22. The surgical tool of claim 21, wherein the locking surface is approximately V-shaped.

23. The surgical tool of claim 19, wherein the hole is sized such that limited or no contact occurs between the locking surface and the inner member when the arms are squeezed toward one another to a fully squeezed position.

24. The surgical tool of claim 19, wherein the hole is sized such that frictional contact with the inner member occurs when the arms are squeezed toward one another to a fully squeezed position, so that the inner member may be locked in both an unsqueezed position and the fully squeezed position of the arms.

25. The surgical tool of claim 19, further comprising a tab formed on the finger, and wherein the tab interlocks the arms to hold the arms in a partially closed position.

26. The surgical tool of claim 19, wherein the lock includes a spring for holding the lock in a biased, locking position.

* * * * *